United States Patent [19]
Rothe et al.

[11] Patent Number: 5,268,269
[45] Date of Patent: Dec. 7, 1993

[54] SCLEROPROTEIN AND SCLEROPROTEIN HYDROLYSATE CONTAINING AGENT FOR DETECTION OF CHOLESTEROL

[75] Inventors: Anselm Rothe, Birkenau; Heino Eikmeier, Lorsch, both of Fed. Rep. of Germany

[73] Assignee: Boehringer Mannheim GmbH, Mannheim, Fed. Rep. of Germany

[21] Appl. No.: 640,651

[22] Filed: Jan. 14, 1991

[30] Foreign Application Priority Data

Jan. 17, 1990 [DE] Fed. Rep. of Germany ....... 4001155

[51] Int. Cl.$^5$ .......... C12Q 1/60; C12Q 1/00; C12Q 1/44; A61R 37/12
[52] U.S. Cl. ........................... 435/11; 435/4; 435/19; 435/805; 530/353; 530/356
[58] Field of Search ............ 435/11, 810, 805, 4, 435/28, 19, 25; 436/13, 71, 166; 530/353, 356

[56] References Cited

U.S. PATENT DOCUMENTS

| | | | |
|---|---|---|---|
| 4,312,834 | 1/1982 | Vogel et al. | 422/56 |
| 4,477,575 | 10/1984 | Vogel et al. | 436/170 |

OTHER PUBLICATIONS

CA 104 (5):31351k, Trasch et al. (1985).

*Primary Examiner*—Michael G. Wityshyn
*Assistant Examiner*—Ralph Gitomer
*Attorney, Agent, or Firm*—Felfe & Lynch

[57] ABSTRACT

The present invention provides a diagnostic agent for the enzymatic determination of cholesterol, wherein, besides the necessary enzymes, it contains a scleroprotein or a scleroprotein hydrolysate; said invention also provides a process for the production of a reagent film for the detection of cholesterol, as well as a test strip for the detection of cholesterol; and said invention is also concerned with the use of scleroproteins and scleroprotein hydrolysates for increasing the enzyme stability in diagnostic agents for the detection of cholesterol and for increasing the temperature-independence of the detection of cholesterol with diagnostic agents.

12 Claims, 1 Drawing Sheet

SCLEROPROTEIN AND SCLEROPROTEIN HYDROLYSATE CONTAINING AGENT FOR DETECTION OF CHOLESTEROL

FIELD OF INVENTION

The present invention is concerned with a diagnostic agent for the enzymatic determination of cholesterol; with a process for the production of a reagent film for the detection of cholesterol; with the use of scleroproteins and of scleroprotein hydrolysates for the improvement of diagnostic agents; and with a process for the determination of cholesterol.

BACKGROUND OF THE INVENTION

To an increasing extent, the determination of analytes in blood is carried out by patients themselves without consulting a physician, the use of test strips thereby having proved to be especially suitable. A prerequisite for the success of such systems used by the patients is the satisfactory function of the test strips, as well as a simple handling thereof. Objective results which are independent of the person carrying out the determination can, in practice, only be obtained by means of a measurement device.

In the case of monitoring the lipid state, the direct determination of the cholesterol concentration by the patients is being increasingly employed. For this purpose, diagnostic agents are generally used which contain the reagents necessary for the detection in the form of a film on a test strip. The production of such a reagent film is described, for example, in U.S. Pat. No. 4,312,834 the entire disclosure of which is incorporated herein by reference.

However, because of the great temperature dependency of biochemical reactions, there is a marked dependency of most detection reactions used in clinical chemistry on the temperature of the surroundings. Therefore, for the avoidance of temperature-dependent falsifications of the analytical results, working is generally carried out at a constantly maintained temperature, for example by means of a tempered adaptor of the measurement device. However, for the success of such systems used by the patients, it is desirable to have a measurement device which is as small as possible and which is also inexpensive. However, only a very approximate and insufficient tempering of the test carrier is possible with such small devices.

Therefore, it is an object of the present invention to provide diagnostic agents for the substantially temperature-independent determination of cholesterol. Further objects and advantages achieved by the present invention will become readily apparent to persons skilled in the art from the following discussion.

SUMMARY OF THE INVENTION

Figure 1:
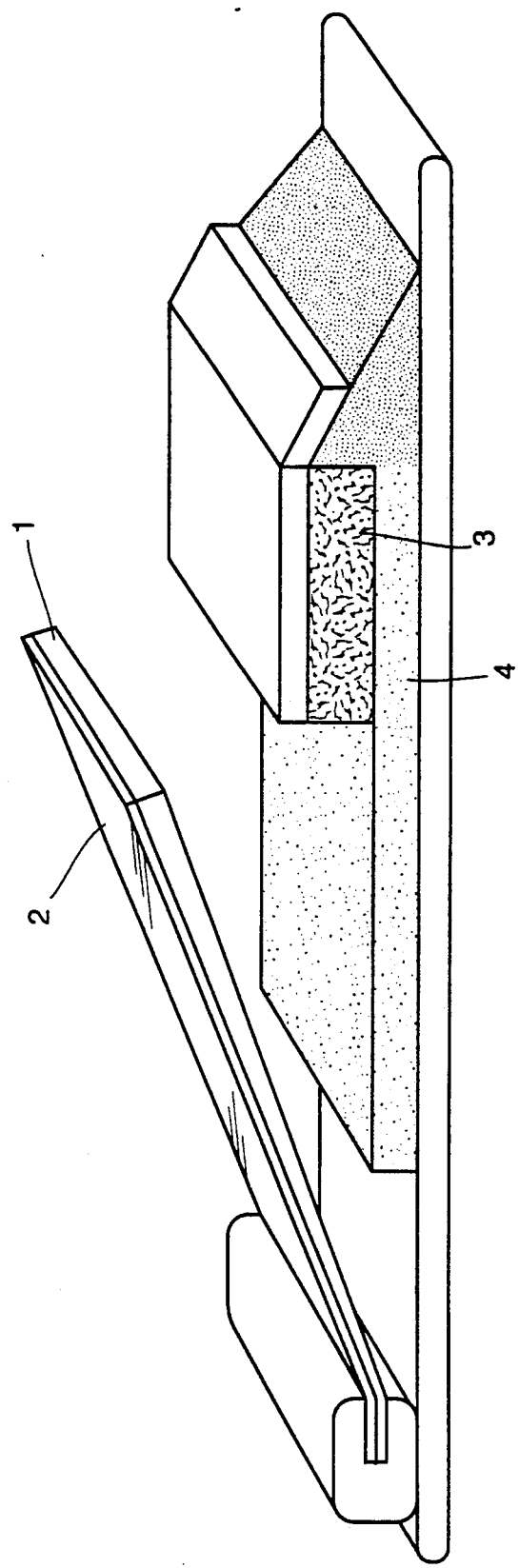
FIG. 1 illustrates a test strip in acordance with the invention for the determination of cholesterol.

In accordance with the present invention, there is provided a diagnostic agent for the enzymatic determination of cholesterol, wherein, besides the necessary enzymes, it contains a scleroprotein or a scleroprotein hydrolysate.

Detailed Discussion

Diagnostic agents for the enzymatic detection of cholesterol are known, for example, from U.S. Pat. No. 4,312,834. These agents preferably contain an enzymatic redox system for the oxidation of the cholesterol. The extent of the oxidation of the cholesterol can be determined via a colour-formation reaction or electrochemically. The preferred main components of a diagnostic agent which comprises a cholesterol oxidase- and cholesterol esterase-containing film mass can be seen from U.S. Pat. No. 4,312,834.

Besides the usual reagents, the diagnostic agent according to the present invention contains a scleroprotein or a scleroprotein hydrolysate. Especially preferred are scleroprotein hydrolysates from collagen or elastin with a molecular weight of from about 1000 to 15,000. Especially preferred is crotein C with a molecular weight of about 10,000.

An especially preferred embodiment of the diagnostic agent according to the present invention contains a film former, for example, polyvinyl propionate, a mineral carrier material, for example, kieselguhr and titanium dioxide, an appropriate pH buffer, cholesterol oxidase, cholesterol esterase, peroxidase and a redoxactive chromogen, for example tetramethylbenzidine. A reagent film with this composition is preferably used as reagent film in U.S. Pat. No. 4,477,575, the entire disclosure of which is incorporated herein by reference. In the test strips, the reagent film is preferably applied to a foil of synthetic material.

For the production of a reagent film, the scleroprotein or scleroprotein hydrolysate is added to the raw film mass, such as is known, for example, from U.S. Pat. No. 4,312,834, in a concentration of from 1 to 5% by weight and preferably of from 2 to 3% by weight, referred to the total weight. Subsequently, the mass is coated, preferably on to a foil of synthetic material, and dried.

We have ascertained that the use of scleroproteins or scleroprotein hydrolysates in enzyme-containing diagnostic agents for the detection of cholesterol increases the stability of the enzymes. In particular, however, by means of the use of scleroproteins or scleroprotein hydrolysates, there is achieved a substantial temperature-independence of the detection of cholesterol in enzyme-containing diagnostic agents. This permits at least a limitation to an inexpensive approximate tempering in the measuring device.

The present invention also provides a process for the determination of cholesterol with the use of a reagent film in which the reagent film contains the above-mentioned scleroproteins or scleroprotein hydrolysates. For this purpose, a liquid sample, for example blood, urine, serum or saliva, but preferably serum, is brought into contact with a reagent film which contains the reagents necessary for the determination of cholesterol and the additives according to the present invention. By means of the reagents, the cholesterol is liberated and oxidized and the reaction product thereby formed is detected via a colour reaction. The reaction with peroxidase and tetramethylbenzidine is here especially preferred. The cholesterol contained in the sample can be quantitatively determined via the resultant colour, the intensity of which is proportional to the amount of cholesterol, optically or preferably by means of a measurement device. The detection can also take place remissionphotometrically in the manner described in European Patent Specification No. A-0,075,766.

FIG. 1 of the accompanying drawing shows a test strip for the determination of cholesterol which contains a reagent film 1 according to the present invention on a transparent carrier foil 2. A sample is applied to the test strip on the right side so that it flows through a fleece 3 for the separation of erythrocytes and collects in a transport fleece 4. The determination reaction is initiated by pressing the carrier foil with the reagent film on to the transport fleece. The coloration of the reagent film is observed through the carrier foil.

The following Examples are given for the purpose of more fully illustrating the present invention. It is to be understood, however, that these Examples are for illustrative purposes only and are not intended to limit the scope of the specification or the claims, or the spirit thereof, in any way.

EXAMPLE 1.

Temperature-Dependence of a Cholesterol Test with the Addition of Ficoll 70D

1. Production of a Reagent Film.

Analogously to European Patent Specification No. A-0,016,387, a film coating mass is prepared with the following components:

- 20 g. 50% polyvinyl propionate dispersion (Propiofan 70 D, BASF)
- 20 g. kieselguhr (Eagle-Pichler Industries, U.S.A.)
- 3 g. titanium dioxide (Kronos-Titan, Leverkusen)
- 10 g. 1% Kelzan solution (Alginate Industries, Hamburg)
- 20 g. phosphate buffer (pH 6.4)
- 10 g. water
- 0.5 g. tetramethylbenzidine (Boehringer Mannheim GmbH)
- 1.0 g. dioctyl sodium sulphosuccinate (Sigma-Chemie, Deisenhofen)
- 0.25 g. 2.5% gallic acid in methanol (Merck, Darmstadt)
- 5 g. tetrahydrofuran, analytical grade (Merck, DArmstadt)
- 10 KU cholesterol oxidate (E.C.1.1.3.6) (Boehringer Mannheim GmbH)
- 40 KU cholesterol esterase (E.C.3.1.1.13) (Boehringer Mannheim GmbH)
- 250 KU peroxidase (E.C.1.11.1.7) (Boehringer Mannheim GmbH)
- 2.5 g. Ficoll 70D (co-polymer of sucrose and epichlorohydrin, Serva)

The film mass is coated with a wet film thickness of 0.2 mm. on to a transparent polycarbonate foil of 0.2 mm. thickness (Lonza, Whyl) and dried at 60° C.

2. Assembly of a Test Strip

The reagent film is assembled to give a test strip according to FIG. 1 of the accompanying drawings.

3. Measurement

The measurements are carried out with the use of a reflection photometer for cholesterol test strips, for example a Reflotron device (Boehringer Mannheim GmbH), as described in European Patent Specification No. B-0,075,766.

Measurement wavelength:
660 nm.; variable tempering of the test strip adaptor of 30° to 50° C.

Measurement Cycle

1st phase: 60 seconds obtaining of plasma and tempering

2nd phase: 14 seconds pressing of the flap 2 with the reagent film 1 on to the transport fleece 4, wetting, starting 3rd phase: 80 seconds, opening, aeration, reaction 4th phase: 4 seconds, pressing on, remission measurement 4. Results The measurement results are summarized in the following Table 1. There can be seen an almost (reciprocal) linear dependency of the measurement signal on the temperature.

TABLE 1

| Temperature-dependence of a cholesterol test with the addition of Ficoll 70 D | | | | | | |
|---|---|---|---|---|---|---|
| temperature of the adapter °C. | | 33.0 | 35.5 | 38.0 | 39.5 | 45.5 |
| serum cholesterol (mg./dl.) | | | | | | |
| 150 | % remission | 54.8 | 55.8 | 58.3 | 59.0 | 64.2 |
|  | % VC | 0.9 | 2.1 | 2.0 | 3.0 | 1.4 |
| 230 | % remission | 31.1 | 31.9 | 33.4 | 34.6 | 39.0 |
|  | % VC | 3.3 | 1.2 | 2.6 | 2.9 | 2.4 |
| 410 | % remission | 18.4 | 18.9 | 19.7 | 20.2 | 24.1 |
|  | % VC | 2.4 | 2.5 | 3.8 | 4.9 | 3.1 |

The variation coefficient (VC) is determined by 10 measurements per temperature and per concentration.

EXAMPLE 2

Temperature-Dependence of a Cholesterol Test with the Addition of crotein C

1. Production of a Reagent Film

The formulation of the film coating mass is as described in Example 1 but with 2.5 g. crotein C (Croda, Nettetal) instead of Ficoll 70 D.

2. Build-Up of the Test Strip

As in Example 1.

3. Measurement

As in Example 1.

4. Results

The measurement results are summarised in the following Table 2. A dependency of the measurement value upon the temperature first occurs above about 40° C. No influencing is shown in the range of from 30° to 40° C. The result permits a limitation to an inexpensive approximate tempering in the measurement device.

TABLE 2

| Temperature-dependence of a cholesterol test with the addition of crotein C | | | | | | |
|---|---|---|---|---|---|---|
| temperature of the adapter °C. | | 33.0 | 35.5 | 38.0 | 39.5 | 45.5 |
| serum cholesterol (mg./dl.) | | | | | | |
| 150 | % remission | 65.5 | 65.4 | 65.4 | 65.1 | 66.3 |
|  | % VC | 0.8 | 0.5 | 0.9 | 0.6 | 0.5 |
| 230 | % remission | 42.2 | 42.0 | 41.8 | 43.1 | 48.8 |
|  | % VC | 1.9 | 2.0 | 2.0 | 1.5 | 2.2 |
| 410 | % remission | 24.9 | 23.9 | 23.7 | 24.4 | 27.3 |
|  | % VC | 1.8 | 1.5 | 1.9 | 3.1 | 1.5 |

The VC is here better than in the case of the use of Ficoll.

What is claimed is:

1. A diagnostic agent effective for the enzymatic determination of cholesterol and comprising enzymes selected from the group consisting of cholesterol oxidase and cholesterol esterase and present in cholesterol determining amounts, and a protein selected from the group consisting of a scleroprotein and scleroprotein hydrolysate, and wherein said protein is present in an amount effective to increase the temperature independence of said detection of cholesterol.

2. The diagnostic agent of claim 1 which contains scleroprotein hydrolysate from collagen or elastin having a molecular weight of from about 1000 to about 15,000.

3. The diagnostic agent of claim 2 wherein said scleroprotein hydrolysate is crotein C having a molecular weight of about 10,000.

4. A process for the production of a reagent film for the detection of cholesterol from a film mass comprising an enzyme selected from the group consisting of cholesterol oxidase and cholesterol esterase and present in cholesterol determining amounts, wherein 1 to 5% by weight of a protein selected from the group consisting of a scleroprotein and scleroprotein hydrolysate is added to the film mass in the production of the reagent film.

5. A reagent film for the detection of cholesterol produced by the process according to claim 4.

6. A process for the determination of cholesterol comprising contacting a sample to be analyzed with a reagent film, wherein said reagent film comprises an enzyme selected from the group consisting of cholesterol oxidase and cholesterol esterase present in cholesterol determining amounts, and wherein said reagent film also contains a protein selected from the group consisting of a scleroprotein and scleroprotein hydrolysate, and wherein said protein is present in an amount effective to increase the temperature independence of said detection of cholesterol.

7. A test strip for the detection of cholesterol which comprises a reagent film containing cholesterol oxidase and cholesterol esterase present in cholesterol determining amounts, and wherein said reagent film also contains a protein selected from the group consisting of scleroprotein and scleroprotein hydrolysate, and wherein said protein is present in an amount effective to increase the temperature independence of said detection of cholesterol.

8. A diagnostic reagent film composition for the enzymic determination of cholesterol comprising,
   a film former present in a film forming amount;
   a suitable reagent film carrier material present in an effective carrying amount;
   a pH buffer;
   cholesterol oxidase;
   cholesterol esterase;
   peroxidase wherein said cholesterol oxidase, cholesterol esterase and peroxidase are present in cholesterol determining amounts;
   a redox active chromogen present in an effective chromogenic amount; and
   a protein selected from the group consisting of scleroprotein and scleroprotein hydrolysate and present in an amount effective to increase the temperature independence of said detection of cholesterol.

9. A test strip comprising a carrier material having the diagnostic reagent film composition of claim 8 fixed thereon.

10. A process for the determination of cholesterol with a reagent film composition comprising contacting a liquid sample to be analyzed with the composition of claim 8.

11. The process of claim 10 wherein said liquid sample contains cholesterol and upon contacting said sample with said reagent film composition said cholesterol is liberated and oxidized thereby forming a detectable color.

12. A process for the detection of cholesterol comprising contacting a sample to be analyzed with an enzyme selected from the group consisting of cholesterol oxidase and cholesterol esterase in cholesterol determining amounts in the presence of a protein selected from the group consisting of scleroprotein and scleroprotein hydrolysates and present in amounts effective to increase the temperature independence of said detection of cholesterol.

* * * * *